United States Patent [19]

Lavens et al.

[11] Patent Number: 5,158,788
[45] Date of Patent: Oct. 27, 1992

[54] FEED FOR AQUACULTURE

[75] Inventors: Patrick Lavens, Torhout; Peter Coutteau, Gent; Patrick Sorgeloos, Zwalm; Erick Vandamme, Gent, all of Belgium

[73] Assignee: Synfina-Oleofina, S.A., Belgium

[21] Appl. No.: 474,849

[22] PCT Filed: Mar. 9, 1989

[86] PCT No.: PCT/BE89/00009
§ 371 Date: Oct. 1, 1990
§ 102(e) Date: Oct. 1, 1990

[87] PCT Pub. No.: WO89/08699
PCT Pub. Date: Sep. 21, 1989

[30] Foreign Application Priority Data

Mar. 9, 1988 [FR] France .................... 88 03034

[51] Int. Cl.$^5$ ................................. A23K 1/00
[52] U.S. Cl. ......................... 426/2; 426/60; 426/62; 119/3; 119/4
[58] Field of Search ............... 426/2, 60, 62; 119/2, 119/3, 4

[56] References Cited

U.S. PATENT DOCUMENTS

| | | | |
|---|---|---|---|
| 3,939,279 | 2/1976 | Kawano et al. | 426/60 |
| 4,640,227 | 2/1987 | Blancheton et al. | 119/2 |
| 4,906,479 | 3/1990 | Kitagawa et al. | 426/60 |
| 4,931,291 | 6/1990 | Kojima et al. | 426/2 |
| 5,047,250 | 9/1991 | Prieels et al. | 426/2 |

OTHER PUBLICATIONS

Prieels et al "Production of fish food compositions" Derwent Abstract C87-006636 of EP 209510 published Jan. 21, 1987.

Kidby et al "Invertase & Disulphide Bridges in the Yeast Wall" *Journal of General Microbiology* (1970) pp. 61 and 327-333.

"Matty et al Evaluation of a Yeast, a Bacterium & an algae as a protein source for rainbow trout" Aquaculture vol. 14 (1978) pp. 235-246.

Douillet "Effect of Bacteria on the Nutrition of Brine Shrimp Artemia Fed on Dried Diets" Artemia Research and its Applications 1987 vol. 3 Universa Press Wetteren Belgium pp. 295-308.

McLellan et al "Phosphomannanase, an Enzyme Required for the Formation of Yeast Protoplasts" Journal of Bacteriology Mar. 1968 pp. 967-974.

Davis "Factors Influencing Protoplast Isolation" Fungal Protoplasts, Applications in Biochemistry & Genetics Marcel Dekker Inc Publishers New York (1985) pp. 45-71.

Murray et al "Nitrogen Utilization in Rainbow Trout Fingerlings Fed Mixed Microbial Biomass" Aquaculture vol. 54 (1986) pp. 263-275.

*Primary Examiner*—R. B. Penland
*Attorney, Agent, or Firm*—Roger W. Parkhurst; Michael J. Caddell; John K. Abokhair

[57] ABSTRACT

The present invention relates to a process for preparing highly digestible feed that may be used among others as feed for aquaculture, by a yeast treatment characterized in that yeast cells are processed to hydrolyze at least partially the external layer of the cell wall without damaging the wall itself.

20 Claims, No Drawings

FEED FOR AQUACULTURE

The present invention relates to a new process for preparing a feed that may be used in aquaculture.

More particularly, the present invention relates to a process for preparing a feed highly digestible by molluscs and crustaceans, by their larvae and juveniles, as well as by the aquatic invertebrates that form their feed.

The development of aquaculture has led many teams to study the feeding of juveniles and of aquatic larvae.

The feed of these animals has two origins:
microscopic algae or micro-algae;
microscopic invertebrates (e.g. Artemia, rotifers) that themselves eat micro-algae.

Micro-algae thus form the first link of the food chain in aquatic environment.

Those algae are, however, not easily available. They must be grown intensively and this contributes to a significant increase in the production costs of aquaculture products.

It would thus be particularly advantageous to be able to replace micro-algae by a substitute product.

Such substitute should have a high nutritive value, and it should not alter the water characteristics.

Moreover, it must satisfy the predator's requirements, i.e. it must have a size such that it can be swallowed in one piece without fracture (while not having a pulverulent consistency), it must be appetizing, and it must be digestible.

Recent research works have led to the development of micro-encapsulated feeds (such as CAR of Frippak-United Kingdom); however these products find a delicate and limited use because of their very high manufacturing cost and because a portion of the nutrients escape from the microcapsule.

Another micro-algae substitute consists of proteins of unicellular origin (Single Cell Protein, or SCP) and more particularly of yeasts.

These products are presently used in the formulation of some feeds, among others for cattle.

Although this type of SCP-based product has recently been relatively popular, its use encounters difficulties arising more particularly from its digestibility which is rather bad. Said bad digestibility implies that before incorporating them into feed for cattle, the cells must be burst, by grinding or thermal treatment.

Such treated product may be used to feed cattle, but it is incompatible with the feeding of animals in aquatic environment. Indeed, the use of such a product leads to an important water pollution which is hardly acceptable.

Experiments made by the assignee have allowed to develop products such as that disclosed in patent application EP-209510-A which uses unburst cells as feed for aquaculture.

Although that product represents an improvement, more particularly for feeding certain shrimp species, it is hardly digested by oyster larvae and by Artemia.

No research has up to now succeeded in the preparation of a suitable substitute of micro-algae, i.e. offering the nutritional advantages of micro-algae while being more easily obtainable.

Applicants now propose a process for preparing such a product. More particularly, applicants have now found a process allowing one to obtain a substitute of micro-algae from yeasts.

The process according to the invention allowing one to prepare from yeasts a highly digestible feed, more particularly digestible by molluscs, crustaceans and larvae thereof, is characterized in that the yeast cells are processed to hydrolyze at least partially the external layer of the cell wall without damaging the wall itself.

The process of the invention is particularly suitable for yeasts of the hemiascomyceteae type, the external layer of which contains disulfide bonds. More particularly, it is preferred to use Saccharomyces yeasts, preferably *Saccharomyces cerevisiae*.

Experiments made with reactants hydrolyzing at least partially the external layer of the cell wall, either enzymatically or chemically, have shown that yeast cells thus processed evidenced an improved digestibility although the processed cells retained their integrity.

In a particularly advantageous way, the process according to the invention allows one to obtain yeasts that are accessible to the digestive enzymes of their predators, but the wall of which remains sufficiently intact so that the cell contents does not flow into the water.

Such stability of the highly digestible yeast thus obtained according to the process prevents water pollution by the cell contents.

The process according to the invention may advantageously be carried out with the following steps:
optionally, washing the yeast,
suspending the yeast in a solution containing a reactant capable of hydrolyzing at least partially the external layer of the cell wall,
incubation of the suspension,
optionally, recovering the cells and/or rinsing.

Washing the yeast is generally made with water or, preferably with an aqueous solution of disodium EDTA or of one of its equivalents. The concentration of disodium EDTA is comprised between 30 and 70 mM, preferably equal to about 50 mM. The pH of the EDTA solution is adjusted, preferably with NaOH, to a value between 7 and 12. This washing is not necessary but it often brings a beneficial effect.

Suspending the yeast is preferably carried out in a solution containing an appropriate amount of a reactant capable of hydrolyzing at least partially the external layer of the cell wall without damaging the wall itself. That solution may also contain from 30 to 70 mM, preferably 50 mM, of disodium EDTA or of one of its equivalents. The pH of that solution is adjusted, preferably with NaOH, to a value between 7 and 12, preferably at about 9. It has been observed that, when using a reactant hydrolyzing the disulfide bridges, an increase in pH generally allows one to use a lesser amount of reactant to reach an equivalent result. The solution in which resuspension is carried out may be identical to that used for the washing; the reactant may also be added to the same solution that was used for washing.

As suitable reactants for carrying out the process of the invention, enzymatic reactants may be used, such as for example a mannanase. Suitable enzymes are known to one skilled in the art, as well as the conditions for using them (pH, concentration, temperature, duration of the incubation). However, these reactants are usually expensive, and chemical reactants are thus preferably used, more particularly those capable of hydrolyzing at least partially the disulfide bridges of the external layer of the cell wall.

Among those reactants, there may be used thiols, preferably mercaptoalcohols, among which mercaptoethanol and dithiothreitol are the most preferred. It can be envisaged to use the alcoholates or thioalcoholates of these compounds.

Also among those reactants, there may be used certain sulfur-containing amino acids, such as cystein or methionin, preferably cystein.

Finally, there may also be used other reducing agents such as soluble sulfides, preferably sodium sulfide ($Na_2S$).

The minimum amount required to observe an effect obviously depends on the incubation conditions (pH, temperature, duration), while adding an excess of chemical reactant is generally avoided for obvious reasons. Thus, these chemical reactants are generally used at a concentration of 0.002 to 1M, preferably of 0.003 to 0.75M when a thiol is used and of 0.01 to 0.1M when an amino acid or another chemical reactant is used.

Very good results are obtained with 5 vol % mercaptoethanol at pH 9.

The suspended yeast thus obtained is recovered by centrifugation or by any other equivalent means, and rinsed at least once, preferably three times, with fresh water or with seawater, to eliminate any trace of reactant.

The cells thus obtained may be stored during at least one week at a temperature near 4° C. in the water of the last rinse, without observing lysis of the cell wall.

The yeast treated according to the process may be used as such as feed for aquaculture, but they are particularly suitable for molluscs and crustaceans, including in their various states of development.

They may also be used as feed for small invertebrates which themselves serve as live feed for the animals hereabove cited. This is the case, for example, for Artemia and rotifers.

They may further be used as starting product for manufacturing a feed for aquaculture according to the process disclosed in patent application EP-209510-A. In that case, cystein is preferably used as reactant, when the addition of oil can advantageously be made directly into the suspension, at the end of the incubation.

The process according to the invention thus allows one to prepare micro-algae substitution products highly digestible by rotifers, molluscs and crustaceans and by larvae thereof. It is a process that is easy to carry out and that uses low cost and easy to find starting materials.

Other characteristics and advantages of the present invention will appear when reading the following examples.

EXAMPLE 1

Comparison between the results of growing Artemia with a standard feed and with a yeast modified according to the process of the invention.

All breedings were made under the same physical conditions, in the same artificial seawater.

a. Preparation of the artificial seawater

The seawater used for the breeding is prepared according to the following known composition:

| | |
|---|---|
| NaCl | 239.0 g |
| $MgCl_2.6H_2O$ | 108.3 g |
| $CaCl_2$ (anhydrous) | 11.5 g |
| $SrCl_2.6H_2O$ | 0.04 g |
| KCl | 6.82 g |
| KBr | 0.99 g |
| $NaSO_4.10H_2O$ | 90.6 g |
| $NaHCO_3$ | 0.20 g |
| NaF | 0.003 g |
| $H_3BO_3$ | 0.027 g |
| distilled water | 9560 ml | b. Preparation of the yeast

The process was applied to fresh baker's yeast *Saccharomyces cerevisiae* (Gist & Spiritusfabrieken Bruggeman, N.V.).

The following steps were taken:
washing of the yeast with a solution of EDTA $Na_2$ (50 mM) in distilled water, the pH of which was adjusted to 8 with NaOH,
adding 2 vol % mercaptoethanol to the hereabove described solution,
resuspending the yeast in the solution thus obtained, at 500 mg/ml (wet weight),
incubating at 30° C. during 30 minutes, recovering the cells using centrifugation,
washing with seawater, three times.

c. Breeding conditions

Dry cysts of Artemia (Great Salt Lake strain), crustaceans of the Anostracean sub-class, were hydrated in artificial seawater at 25° C. under constant lighting.

The nauplii were harvested after 24 hours incubation and they were placed in Falcon Blue Max 1070 ® tubes, each tube containing 50 ml of seawater aerated using a Pasteur pipette and receiving 25 nauplii.

The breedings lasted for one week. Feed was given daily. On the fourth day, before feeding, fifteen surviving larvae from each tube were transferred into tubes containing fresh artificial seawater.

d. Carrying out of the breedings

The tubes were divided into four series, bred together under the same conditions, except for the daily feed:
yeast obtained by the process of the invention, as carried out in this example, was fed to one Artemia breeding,
another Artemia breeding was made with the same yeast but which was not processed,
a third breeding was made with protoplast of the same strain of *Saccharomyces cerevisiae* obtained by routine procedures,
a fourth breeding (which may also serve as internal standard to compare successive breedings) was made with a living unicellular micro-algae Dunalliela tertiolecta known to be a suitable feed for Artemia.

e. Results

On the fourth day (before the transfer) and on the eighth day, the following parameters were determined:
$X_s$: average percentage of surviving larvae
$S_s$: standard deviation on $X_s$
$X_c$: average length of the larvae, expressed in mm
$S_c$: standard deviation on $X_c$
n: for each type of feed, number of tubes for which the preceding values were determined,
knowing that:
100% survival on 4th day = 25 larvae per tube
100% survival on 8th day = 15 larvae per tube.

The length of the larvae was measured using a binocular microscope equipped with a drawing mirror.

The results are mentioned in Table 1 hereafter.

TABLE 1

| Feed | Survival | | | Length | | |
|---|---|---|---|---|---|---|
| | $X_s$ | $S_s$ | n | $X_c$ | $S_c$ | n |
| *4th day* | | | | | | |
| Protoplast | 86 | 8 | 29 | 1.77 | 0.10 | 6 |
| Raw yeast | 72 | 15 | 11 | 1.31 | 0.06 | 6 |
| Processed yeast | 81 | 7 | 12 | 1.63 | 0.17 | 6 |
| Micro-algae | 94 | 7 | 5 | 1.80 | 0.15 | 5 |
| *8th day* | | | | | | |
| Protoplast | 67 | 14 | 12 | 3.98 | 0.31 | 6 |
| Raw yeast | 29 | 8 | 5 | 2.91 | 0.10 | 5 |
| Processed yeast | 68 | 13 | 6 | 4.63 | 0.26 | 6 |
| Micro-algae | 95 | 6 | 5 | 4.24 | 0.18 | 5 |

The performance of the yeast protoplast are good, showing that the yeast cell content is a good feed for Artemia.

The performances of raw yeast are weak, because the cell wall prevents digestion of the cell content.

The performances of processed yeast are nearly as good as those of protoplast without having the inconvenience thereof (water pollution).

Yeast treated according to the process thus combines the advantages of protoplast for the nutritive value with those of raw yeast for the innocuousness towards the water.

EXAMPLE 2

Comparison between Artemia breeding results with yeasts treated according to various embodiments of the process of EXAMPLE 1.

a. Yeast preparation

Two batches of the same yeast as that used in EXAMPLE 1 were subjected to two embodiments of the process:

First embodiment the pH of the EDTA $Na_2$ solution was adjusted to 9 with NaOH,
to that solution was added 5 vol % mercaptoethanol when resuspending the yeast.

Second embodiment the pH of the EDTA $Na_2$ solution was adjusted to 12 with NaOH,
to that solution was added 0.02 vol % mercaptoethanol when resuspending the yeast.

b. Carrying out of the breedings

All breeding conditions were the same as those described in EXAMPLE 1.

The tubes were divided into five series, bred together under the same conditions, except for the daily feed:
one breeding was made with raw yeast,
a second breeding was made with yeast as modified in EXAMPLE 1,
a third breeding was made with yeast as modified according to the first embodiment described hereabove,
a fourth breeding was made with yeast as modified according to the second embodiment described hereabove,
finally, a control breeding was made with the micro-algae used in EXAMPLE 1.

c. Results

The growth and survival results on the 4th day (before transfer) and on the 8th day are grouped in Table 2 hereafter.

TABLE 2

| Feed | Survival | | | Length | | |
|---|---|---|---|---|---|---|
| | $X_s$ | $S_s$ | n | $X_c$ | $S_c$ | n |
| *4th day* | | | | | | |
| Raw Yeast | 85 | 7 | 6 | (1.16) | — | — |
| Yeast processed according to example 1 | 96 | 5 | 6 | (1.82) | — | — |
| Yeast processed according to the 1st embodiment | 95 | 5 | 6 | (1.87) | — | — |
| Yeast processed according to the 2nd embodiment | 99 | 2 | 6 | (1.49) | — | — |
| Micro-algae | 98 | 2 | 5 | (2.04) | — | — |
| *8th day* | | | | | | |
| Raw Yeast | 31 | 17 | 6 | 1.69 | 0.22 | 6 |
| Yeast processed according to example 1 | 66 | 15 | 6 | 4.76 | 0.25 | 6 |
| Yeast processed according to the 1st embodiment | 74 | 7 | 6 | 4.91 | 0.24 | 6 |
| Yeast processed according to the 2nd embodiment | 67 | 12 | 6 | 4.68 | 0.13 | 6 |
| Micro-algae | 93 | 9 | 5 | 4.37 | 0.30 | 5 |

Better performances were observed with yeast treated according to the embodiments described in example 2, particularly in the case of the second embodiment that uses very low mercaptoethanol concentrations at high pH.

EXAMPLE 3

Comparison between results of Artemia breeding with yeasts treated with amino acids and with reducing agents.

a. Yeast preparation

Two embodiments of the process were applied to two series of the same yeast as that used in example 1.

First embodiment cystein was added at a concentration of 0.1M to the EDTA $Na_2$ solution,
the pH of the solution was adjusted to 8, when resuspending the yeast.

Second embodiment the pH of the EDTA $Na_2$ solution was adjusted to 9 with NaOH,
when resuspending the yeast, 0.1M of sodium sulfide ($Na_2S$) was added to that solution.

b. Carrying out of the breedings

All the breeding conditions were the same as those described in example 1.

The tubes were divided into five batches, bred together under the same conditions, except for the daily feed:
one breeding was made with yeast as modified in the first embodiment of example 2,
a second breeding was made with yeast as modified according to the first embodiment of this example, a third breeding was made with yeast as modified according to the second embodiment of this example.

c) Results

| Feed: processed yeast | Survival | | | Length | | |
|---|---|---|---|---|---|---|
| | $X_s$ | $S_s$ | n | $X_c$ | $S_c$ | n |
| | 4th day | | | | | |
| according to example 2 (1st embodiment) | 97 | 6 | 6 | (1.49) | — | — |
| according to example 3 (1st embodiment) | 91 | 5 | 6 | (1.76) | — | — |
| according to example 3 (2nd embodiment) | 95 | 4 | 6 | (1.58) | — | — |
| | 8th day | | | | | |
| according to example 2 (1st embodiment) | 76 | 11 | 6 | 4.17 | 0.36 | 6 |
| according to example 3 (1st embodiment) | 70 | 12 | 6 | 4.07 | 0.65 | 6 |
| according to example 3 (2nd embodiment) | 41 | 14 | 6 | 4.61 | 0.27 | 6 |

In the absence of a control breeding made simultaneously with the micro-algae used in the preceding examples, the results of this example should only be compared between them. They show among other things that the use of cystein is preferable to that of sodium sulfide.

We claim:

1. A process for treating yeast to make it more digestible by mollusks and crustaceans, including their larvae and juveniles, and the aquatic invertebrates forming their feed comprising
   treating the yeast cells with an amount of a chemical or enzyme reactant, which reactant and amount are effective to hydrolyze at least partially the external layer of the wall of the yeast cells without damaging the cell wall itself to give a treated yeast having improved digestibility for use as an aquaculture feed, said treated yeast being accessible to the digestive enzymes of the yeast's predators and having the cell walls sufficiently intact so that the cell contents do not flow into water.

2. The process of claim 1 wherein the yeast is a hemiasomyceteae-type yeast.

3. The process of claim 1 wherein the yeast is a Saccharomyces yeast.

4. The process of claim 1 wherein the yeast cells are treated with a reactant that hydrolyses at least partially the disulfide bridges of the external layer of the cell wall.

5. The process of claim 4 wherein the hydrolysis is carried out enzymatically.

6. The process of claim 4 wherein the hydrolysis is carried out chemically with a reactant selected from the group consisting of a compound having a thiol function, a soluble sulfide, and a mixture thereof.

7. The process of claim 6 wherein the reactant is selected from the group consisting of mercaptoethanol, dithiothreitol, cystein, sodium sulfide, or mixtures thereof.

8. The process of claim 7 wherein the reactant is mercaptoethanol.

9. A process for treating yeast to make it more digestible by mollusks and crustaceans, including their larvae and juveniles, and the aquatic invertebrates forming their feed comprising
   suspending the yeast in an aqueous solution containing a reactant in an amount effective to hydrolyze at least partially the external layer of the cell wall of the yeast, said reactant selected from the group consisting of a compound having a thiol group, a watersoluble sulfide, and mixtures thereof and
   incubating the suspension to give a treated yeast having improved digestibility for use as an aquaculture feed, said treated yeast being accessible to the digestive enzymes of the yeast's predators and having the cell walls sufficiently intact so that the cell contents do not flow into water.

10. The process of claim 9 further comprising washing the yeast before suspending the yeast in an aqueous solution.

11. The process of claim 9 further comprising recovering the yeast after incubating the suspension.

12. The process of claim 11 further comprising rinsing the yeast cells after recovery.

13. The process of claim 9 wherein the yeast is a hemiasomyceteae-type yeast.

14. The process of claim 13 wherein the yeast is a Saccharomyces yeast.

15. The process of claim 9 wherein the reactant is selected from the group consisting of mercaptoethanol, dithiothreitol, cystein, sodium sulfide, and mixtures thereof.

16. The process of claim 15 wherein the reactant is mercaptoethanol.

17. The process of claim 9 wherein the yeast is suspended at 300 to 700 mg/ml on a wet weight basis in an aqueous solution having a pH from about 7 to about 12 and containing from about 0.002 to about 1M of reactant.

18. The process of claim 17 wherein the reactant is a thiol present in an amount from about 0.003 to about 0.75M.

19. The process of claim 17 wherein the reactant is not a thiol and is present in an amount from about 0.01 to about 0.1M.

20. The process of claim 9 wherein incubation is carried out at a temperature of from about 25° C. to about 35° for a period of from about 15 minutes to about 45 minutes.

* * * * *

UNITED STATES PATENT AND TRADEMARK OFFICE
CERTIFICATE OF CORRECTION

PATENT NO. : 5,158,788

DATED : October 27, 1992

INVENTOR(S) : Patrick Lavens; Peter Coutteau; Patrick Sorgeloos; Erick Vandamme

It is certified that error appears in the above-identified patent and that said Letters Patent is hereby corrected as shown below:

On the title page, item [73], change "Synfina-Oleofina, S.A., Belgium" to --Artemia Systems N.V., Belgium--

Signed and Sealed this

Twenty-ninth Day of March, 1994

Attest:

BRUCE LEHMAN

*Attesting Officer*     *Commissioner of Patents and Trademarks*